United States Patent [19]

Tripodi

[11] 4,365,661
[45] Dec. 28, 1982

[54] ENHANCED VAPORIZATION/CONDENSATION HEAT PIPE

[75] Inventor: Robert Tripodi, Warehouse Point, Conn.

[73] Assignee: United Technologies Corporation, Hartford, Conn.

[21] Appl. No.: 226,274

[22] Filed: Jan. 19, 1981

[51] Int. Cl.³ ............................................. F28D 15/00
[52] U.S. Cl. ................................... 165/1; 165/104.12; 165/104.21
[58] Field of Search .................. 165/104.12, DIG. 17, 165/104.21–104.27, 1

[56] References Cited

U.S. PATENT DOCUMENTS 308,197  11/1884  Rober .............................. 165/104.12

OTHER PUBLICATIONS

R. L. McKisson, *Dissociation-Cooling: A Discussion*, Livermore Research Laboratory of the A.E.C., Livermore, CA, 3/54, pp. 1–20, LRL-86.
N. G. Aabalu et al., *Chemical Heat Pipe*, IBM Technical Disclosure Bulletin, vol. 13, No. 12, p. 3812, 5/71.

*Primary Examiner*—Albert W. Davis, Jr.
*Attorney, Agent, or Firm*—Stephen A. Schneeberger

[57] ABSTRACT

A method and apparatus for the enhanced transport of thermal energy utilizing a heat pipe operated principally in the vaporization/condensation mode. The heat pipe is a closed circuit fluid circuit having a heat source position and a heat sink position. A transport fluid is selected to enter the heat source position as a liquid, be vaporized thereat and at least partly chemically reacted with the aid of a catalyst, then transported to the heat sink position whereupon a reverse chemical reaction thereof is induced to release heat. Condensation of the transport fluid also occurs at or near the heat sink position and the transport fluid is returned to the heat source position in liquid form. The transport fluid is selected such that for the temperature of operation at the heat source position and for the temperature drop between the source and sink positions, a significant portion of the total thermal energy removed from the heat source, typically upwards of 50 percent, occurs by vaporization prior to the endothermic reaction. The endothermic chemical reaction further enhances the vaporization rate. In one example, the temperature differential between the heat source and heat sink positions is in the range of about 20°–80° K. and the transport fluid is isobutane and its reaction product n-Butane.

19 Claims, 6 Drawing Figures

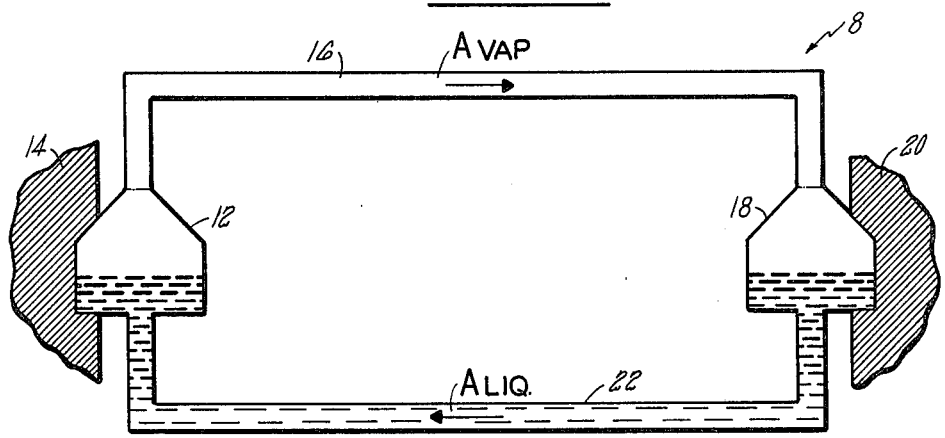
FIG.1 PRIOR ART
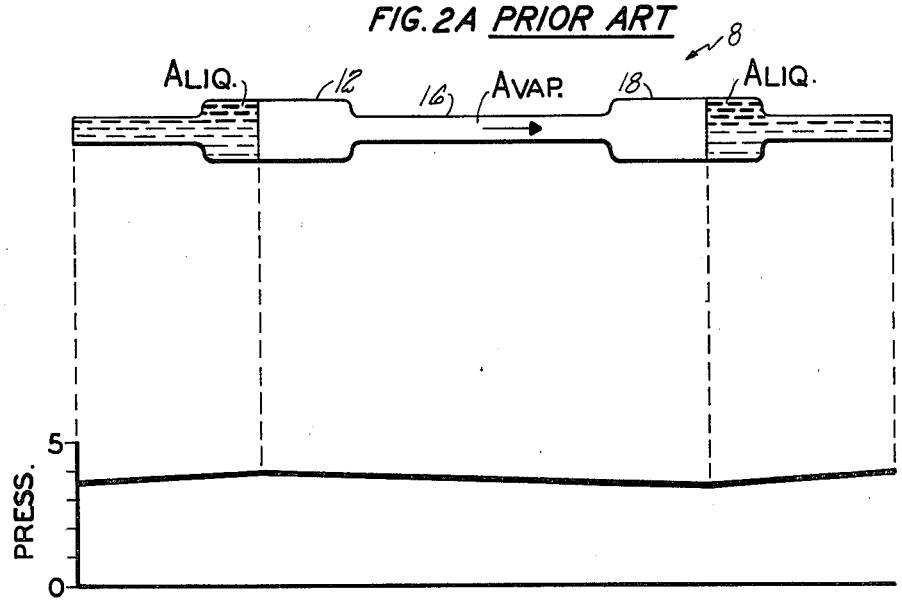
FIG.2A PRIOR ART
FIG.2B PRIOR ART

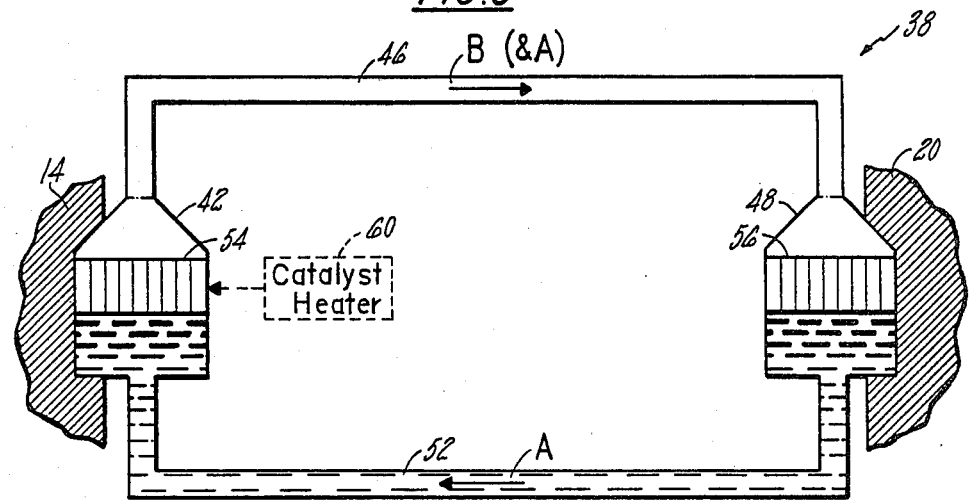
FIG. 3
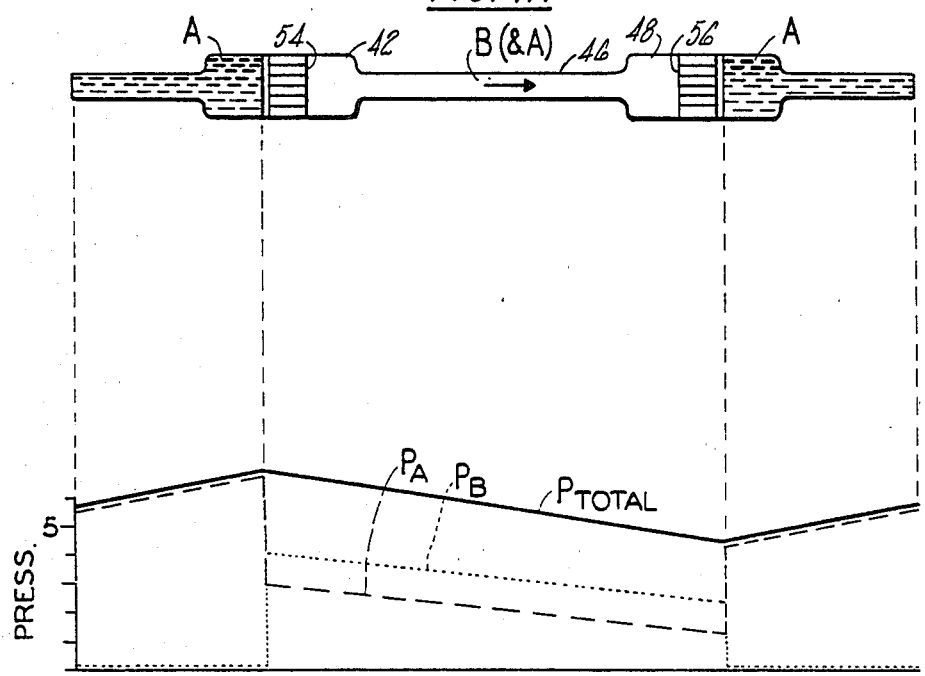
FIG. 4A
FIG. 4B

ENHANCED VAPORIZATION/CONDENSATION HEAT PIPE

TECHNICAL FIELD

The present invention relates to the method of and apparatus for transporting thermal energy and more particularly to the utilization of a heat pipe for the transport of heat. More specifically, the present invention relates to the transport of heat utilizing a vaporization/condensation cycle enhanced by a reversible chemical reaction.

BACKGROUND OF THE INVENTION

Various techniques have been employed for transferring or transporting thermal energy between a thermal source and a thermal sink or load. One technique or means often used employs a heat pipe. The heat pipe is connected between the heat source and the heat sink and a transport medium therewithin is caused to flow between the two positions to transfer thermal energy from the source to the sink. A basic form of heat pipe employs a vaporization/condensation cycle or mode of operation for effecting the requisite thermal energy transfer. In that type of heat pipe, there is rapid heat transfer into the pipe resulting in vaporization of a liquid transport medium therein. The evaporated transport medium builds up sufficient pressure to be transported along the pipe and is then condensed at the heat sink position. The cycle is completed by returning the condensate to the evaporating end by means of capillary or other action through a wick or other suitable means within the pipe. Typically, the working fluid may be water, freon, methyl alcohol, acetone or the like. The heat of vaporization is such that significant quantities of heat may be absorbed during the vaporization of the transport liquid and subsequently released at the heat sink during its condensation.

Because the thermal energy transported in a vaporization/condensation type of heat pipe is transported at the elevated temperatures of the vaporized transport medium, the opportunity for heat loss during transport by radiation, convection and/or conduction may be significant, particularly if the transport distance is greater than tens of feet. In instances in which thermal energy is to be transported relatively long or significant distances, for instance from tens or hundreds of feet to as much as tens or hundreds of miles, and it is desired to minimize thermal losses during transport, chemical heat pipes can be employed. In such heat pipes, a reactant or reactants undergo a first chemical reaction at the heat source and a second chemical reaction at the heat sink. The reactions are generally reversible, with the first being of an endothermic nature in which heat is chemically absorbed by the reaction process and with the second being exothermic in which heat is chemically liberated during the reaction process. The reactant and/or reaction products may exist and be transported at temperatures which do not differ substantially from that of the environment, thereby greatly reducing the potential for thermal loss from the system. In such chemical heat pipes, most of the thermal energy absorbed from the source occurs by virtue of the endothermic reaction, with relatively little heat being absorbed by evaporation. An example of one such chemical heat pipe is disclosed in copending U.S. application Ser. No. 226,320 entitled Self-driven Chemical Heat Pipe by A. S. Kesten and A. F. Haught, filed on even date herewith and assigned to the assignee of the present application.

Although heat pipes of the chemical reaction type may be particularly suited for the long-distance transport of thermal energy, the sometimes simpler and less expensive vaporization/condensation type of heat pipe is used almost exclusively for situations in which the distance over which the thermal energy to be transported is relatively short, for instance less than tens of feet and for those situations in which the source temperature and/or the source-sink temperature difference is insufficient for a suitable chemical heat pipe reaction. The vaporization/condensation type heat pipe is generally self-driven and the rate of thermal energy transport is determined by the transport medium, by the relevant operating temperatures and by the geometry of the system. Generally, the rate of heat transport in a system in which the evaporation and condensation surface areas are relatively small will be less than that for which those surfaces are relatively large, other factors being equal. Various physical constraints and/or cost considerations may however, interfere with or prevent the provision of a vaporization/condensation heat pipe of sufficient physical capacity for the task intended.

Accordingly, it is a principal object of the present invention to provide a heat pipe of the vaporization/condensation type with enhanced operating capabilities. Included in this object is the provision of a method for enhancing the rate of thermal transport in vaporization/condensation heat pipes of particular and limited geometries.

DISCLOSURE OF INVENTION

In accordance with the present invention, there is provided a method and apparatus for the enhanced transport of thermal energy utilizing a heat pipe operated principally in the vaporization/condensation mode. The heat pipe comprises a closed-circuit fluid conduit having a heat source position in heat exchange relation with the heat source and a heat sink position in heat exchange relation with the heat sink. Appropriate catalysts are situated in or near the heat source and heat sink positions of the conduit respectively. A transport fluid within the conduit is selected to enter the heat source position as a liquid, to be vaporized thereat and to be caused to chemically react at least partially, promoted by a catalyst, to thereby provide at least some reaction product. The reaction product and any unreacted vaporized transport fluid are transported to the heat sink position where the reverse chemical reaction is induced by a change of conditions (e.g., lower temperature) and promoted by a suitable catalyst to reform transport fluid, accompanied by the generation of some thermal energy for release to the sink. The transport fluid vapor is condensed at the heat sink position thereby to release thermal energy to the sink and return the transport fluid to the liquid form. The liquid transport fluid is then finally returned to the heat source position for completing and repeating the cycle.

The transport fluid is selected such that for the temperature of operation at the heat source position and for the temperature drop between the source and sink, a significant portion of the total thermal energy removed from the heat source occurs by vaporization of the transport fluid. For example, the vaporization of the transport fluid prior to its endothermic reaction accounts for the absorption of at least 50% of the total thermal energy removed by that fluid and may range upwardly to 80% or more. By reacting the vaporized transport fluid to convert it to a reaction product, the transport fluid vapor is removed from the vicinity of the liquid surface from which it evaporates, thereby tending to enhance the net evaporation rate and thus the rate of heat absorption or transfer from the source.

In one embodiment, the temperature differential between the heat source and heat sink positions is in the range of about 20°–80° K. Isobutane and its reaction product n-Butane are examples of a transport fluid and reaction product respectively which provide the advantages of the invention, especially in heat pipes having size constraints and/or where the distance between the heat source and heat sink is relatively short.

BRIEF DESCRIPTION OF DRAWINGS

FIG. 1 is a diagrammatic representation of a prior art vaporization/condensation heat pipe system;

FIG. 2A is an illustration of certain segments of the heat pipe of FIG. 1, shown aligned for graphical purposes;

FIG. 2B is a graphical plot of the pressure of the transport fluid in the heat pipe segments of FIG. 2A;

FIG. 3 is a diagrammatic representation of the reaction-enhanced vaporization/condensation heat pipe of the invention;

FIG. 4A is an illustration of certain segments of the heat pipe of FIG. 3, shown aligned for graphical purposes; and FIG. 4B is a graphical plot of transport fluid and reaction product pressures in the heat pipe segments of FIG. 4A.

BEST MODE FOR CARRYING OUT THE INVENTION

Referring to FIG. 1, there is diagrammatically illustrated a conventional vaporization/condensation driven heat pipe 8 of the prior art. A volatile liquid transport fluid A is vaporized at a heat source position comprised of an evaporator 12 in heat exchange relation with a heat source 14. The vapor, A vap, flows through conduit 16 to a heat sink position comprised of condenser 18 in heat exchange relation with a heat sink 20. The vaporized liquid is condensed at condenser 18, thereby releasing to the sink 20 most of the heat acquired from the source. Some radiation, conduction and/or convection losses may be experienced, depending in part on the transport distance which is usually restricted to distances of less than tens of feet. The condensate, A liq., travels back to the evaporator 12 through a return conduit 22. The return conduit 22 may include a wick or the like for returning liquid 10 by means of capillary action or the like, as determined by the geometry and orientation of the heat pipe. Vapor movement is sustained by a negative pressure gradient between the source position and the sink position, established by having the condenser 18 at a lower temperature (and hence lower equilibrium pressure) than the evaporator 12.

A limitation on the performance of a heat pipe 8 results from the necessary trade-off among the requirements for efficient vaporization at the source position, condensation at the sink position, and mass transport between them. The vaporization rate in the evaporator 12 is proportional to the difference between the equilibrium pressure of the transport fluid A and its actual vapor pressure (i.e., $(P_e^{eq} - P_e)$). Similarly, the condensation rate is proportional to the difference between the actual condenser pressure and its equilibrium pressure (i.e., $(P_c - P_c^{eq})$). In order to maintain flow from source 14 to sink 20, the evaporator pressure must be greater than the condenser pressure. This leads to the inequality $$P_e^{eq} > P_e > P_c > P_c^{eq}$$

It will be seen that the driving force for either evaporation or condensation is limited to values less than $(P_e^{eq} = P_c^{eq})$. Furthermore, an increase in one of them occurs at the expense of the other. For instance, lowering $P_e$ to increase $(P_e^{eq} - P_e)$ will lead to a smaller $(P_c - P_c^{eq})$ since $P_c$ will be lowered. Hence, if there are constraints on the physical size of heat pipe components, these inequalities among the various pressures limit the possible vaporization/condensation rate and the accompanying heat transport.

FIG. 2A is an illustration of a portion of the prior art heat pipe 8 of FIG. 1, opened at the liquid return conduit 22 and arranged in straightline fashion for the purposes of the graphical presentation of the transport fluid pressure in FIG. 2B. The graph of FIG. 2B depicts the pressure of the transport fluid A of the heat pipe 8 expressed in arbitrary units of pressure and varying as a function of the location of the transport fluid within the heat pipe. Thus, in FIG. 2B, it will be observed that the maximum pressure of the transport fluid occurs in the evaporator 12 just downstream of the liquid-vapor interface therein. The pressure of the transport fluid is at minimum in the condenser 18 substantially at the interface at which it makes the transition from the vapor phase to the liquid phase. The drop in pressure across vapor-phase conduit 16 provides the driving force for the system and a wick may return the liquid-phase transport fluid, A liq, from the condenser 18 to the evaporator 12.

The aforementioned limits on the performance of a conventional vaporization/condensation type of heat pipe can, however, be relaxed and its operation enhanced by the incorporation of a chemical reaction in the cycle. The heat pipe 38 of FIG. 3 represents such a reaction augmented vaporization/condensation type heat pipe. A volatile transport fluid, entering in the liquid phase, is vaporized and reacted at a heat source position comprised of the evaporative reactor 42 in heat exchange relation with heat source 14. The transport fluid is again designated A inasmuch as it may be the same as or may differ from the transport fluid in the aforedescribed vaporization/condensation heat pipe of FIG. 1. The transport fluid A is first vaporized and then immediately endothermically reacted by the catalyst 54 in intimate contact therewith. The product or products, hereinafter referred to as reaction product B, is transported in the gaseous or vapor phase through conduit 46 to the reactor condenser 48. To the extent the reaction in reactor 42 is not complete, some vaporized transport fluid A may also be transported to reactor condenser 48 via conduit 46. The reaction product B is exothermically catalytically reacted by a suitable catalyst 56 in reactor 48 to reform transport fluid A, which transport fluid is then condensed to the liquid phase and returned by a wick or the like through conduit 52 to the evaporator reactor 42 to complete and repeat the cycle.

An important aspect of the above described cycle resides in the removal of the vaporized transport fluid A from the vicinity of the liquid surface of transport fluid A by means of the endothermic reaction in reactor 42. That removal of the vaporized transport fluid A serves to enhance the net evaporation rate of transport fluid A from the liquid supply thereof. In this particular cycle of operation, and for the transport fluids selected, the heat of vaporization and thus the heat absorbed from the heat source by vaporization is greater and generally substantially greater than the heat of reaction. Therefore, this type of enhancement of the net evaporation rate serves to enhance the operation of the heat pipe as a whole.

The essential differences between the reaction augmented vaporization/condensation heat pipe 38 and the conventional heat pipe 8 arises from the fact that the rate of evaporation and condensation depend only on the difference between the equilibrium vapor pressure, $P_A^{eq}$, and the partial pressure of A, $P_A$. Reduction of the partial pressure $P_A$ at the evaporator interface leads to enhanced vaporization. The transport of gas or vapor from the heat source to the heat sink, on the other hand, depends on the difference between the total pressures at each location (i.e. $P_{tote} > P_{totc}$). It is no longer necessary, however, that $P_{Ae} > P_{Ac}$. In principle, it is possible for the partial pressures to be such that $P_{Ae} < P_{Ac}^{eq}$ and $P_{Ac} > P_{Ae}^{eq}$. Thus, the magnitudes of the driving force factors, $(P_{Ae}^{eq} - P_{Ae})$ and $(P_{Ac} - P_{Ac}^{eq})$, can be much larger than would be possible in a conventional case and heat transport can be enhanced.

Reference is made to the following simplified example for an illustration of a basic form of the invention. Assuming that the reaction near the evaporation 42 is instantaneous and goes to completion, and that the reaction near the condenser 48 regenerates a finite amount of transport fluid A, then the partial pressure, $P_{Ae}$, of A at the liquid-gas interface of the evaporator 42 will be zero. Moreover, the evaporization rate will attain it maximum possible value, proportional to $P_{Ae}^{eq}$. The rate of mass addition due to vaporization must balance the mass flow from the source position to the sink position, and the rate of condensation must equal the rate of vaporization. The total pressures at evaporator 42 and condenser 48 will adjust to satisfy these constraints in accord with the equilibrium composition within the condenser reactor 48. An equivalent conventional vaporization/condensation heat pipe (i.e. equivalent temperature and surface areas for evaporation and condensation, and equivalent flow passages between source and sink) will have a finite pressure of transport fluid A at the evaporator 18 interface, rather than zero. Hence, the evaporation rate (and heat transport) will be higher for the reactive case. The correspondingly higher condensation rate means that the pressure, $P_{Ac}$, of transport medium A at the condenser 48 interface, also will be higher for the reactive case. Since $P_{tot} > P_A$ and $P_{tote} > P_{totc}$, the total pressure in condenser 48 will be higher for the reactive case, and generally so will the total pressure in the evaporator 42.

For intermediate cases in which the endothermic reaction is incomplete, the pressures and heat transport values will be intermediate those at the extremes of no reaction (conventional) and complete reaction. The same general relationships will exist for comparisons with the conventional case: (1) heat transport-greater, (2) evaporator partial pressure, $P_{Ae}$-lower, (3) evaporator total pressure, $P_{tote}$-generally higher, (4) condenser total pressure, $P_{totc}$-higher, and (5) condenser partial pressure, $P_{Ac}$-higher.

FIG. 4A illustrates the reaction-enhanced heat pipe 38 of FIG. 3, opened at the liquid return conduit 52 and arranged in straight line fashion for the graphical presentation of the transport fluid pressure and partial pressures depicted in FIG. 4B. The intermediate case described in the immediately foregoing paragraph is portrayed in FIG. 4B in which the total fluid pressure, $P_{total}$, in heat pipe 38 is comprised of a transport fluid A component, $P_A$, (shown in dashed line) and a reaction product component, $P_B$, (shown in dotted line). It will be observed that while the general profile of total pressure, $P_{total}$, is similar, but somewhat higher, than that of the conventional heat pipe 8 depicted in FIG. 2B, the pressure of transport fluid A is rapidly decreased by reaction at catalyst 54. Had an even more complete reaction of transport fluid A occurred, as is possible, the pressure $P_A$ of that fluid could have dropped to near zero and the pressure $P_B$ of reaction product would have similarly increased.

In an ideal case, the reaction augmented that pipe would involve chemistry in which both the transport medium A and the reaction product B are stable, but are easily reversibly reacted by catalytic reaction with only a small temperature change between the source and sink positions. Whereas conventional heat pipes can operate over temperature drops of a few degrees, somewhat higher temperature drops are necessary to realize the significant enhancement afforded by the invention. However, the temperature drops required by the invention, generally in the range of 20°-80° K., are normally significantly below the temperature drops of 100°-200° K. and greater required by classical chemical heat pipes. Heat source position temperatures of 280°-380° K. are representative, but they are by no means limiting and may be lower or substantially higher.

For applications in which efficient cooling is provided to a high temperature device and there is relatively little concern for heat loss during transport, a relatively large temperature drop may be accommodated by the heat pipe of the invention. If, however, the application is the transport of heat while minimizing degradation in its quality, it may be necessary to raise the temperature of the catalyst surfaces in the evaporator reactor 42 (or shift the equilibrium by other means) to promote reaction in the proper direction. If the reaction is not highly energetic only a small penalty on efficieny occurs. Further, note that the reaction augmentation depends more strongly on complete dissociation at the source than on complete recombination at the sink. Thus, smaller temperature differences can be achieved by accepting incomplete recombination in the condenser reactor 48, which will manifest itself primarily as higher total pressure in the system.

The enhanced vaporization/condensation heat pipe 38 of the invention will typically transport most of the heat, i.e. 50-95% or more, as the heat of vaporization of the transport medium, whereas the classical chemical heat pipe typically transports most of the heat, i.e. 50-95% or more, in chemical form via the heat of reaction and the conventional vaporization/condensation heat pipe transports all of the heat as the heat of vaporization.

In accordance with a preferred embodiment of the invention, an exemplary and particularly suitable reaction comprises the isomerization reaction of isobutane. Isobutane is transported as a liquid to evaporator 42 where it is first vaporized and then catalytically endothermically reacted to form reaction product B, in this instance n-butane. Depending on the operating temperatures, the isobutane may be completely reacted or it may be only partially reacted such that some vaporized isobutane is also transported through heat pipe conduit 46 to condenser 48. At condenser 48 the n-butane is catalytically reacted exothermically, liberating some heat to sink 20 and reforming isobutane. The vaporized isobutane is then condensed, releasing an even greater quantity of heat to sink 20, and the resulting liquid isobutane is conducted back to evaporator 42 through conduit 52. A suitable material for catalysts 54 and 56 is aluminum chloride on alumina. The reaction may be expressed as:

$$(CH_3)_2CHCH_3 \rightleftharpoons C_4H_{10}$$

The heat of vaporization of isobutane is about 5 Kcal/mole and the heat of reaction is about 1.6 Kcal/mole, such that more than 70% of the thermal energy absorbed from the heat source is by vaporization of the isobutane even for complete reaction.

Consideration is now given to a series of comparisons between a conventional vaporization/condensation heat pipe (as in FIG. 1) employing isobutane as transport fluid A and a reaction-enhanced vaporization/condensation heat pipe (as in FIG. 3) also employing isobutane as the transport fluid A. These comparisons are expressed in the following table in which a 300° K. sink temperature was assumed for all cases and a total pressure of 8.5 atmospheres (maximum without condensing n-butane) was provided. It was necessary to vary the capacity of the system somewhat to obtain the same pressure in each instance, resulting in the small apparent inconsistencies in the pressures for the conventional case.

the catalyst to the desired temperature. Such additional heat might represent an additional energy cost, but the quantity of that additional heat would normally be small relative to the heat received from the waste heat source and its cost may be minimized if it were usefully recovered at the heat sink. The heat of vaporization remains the dominant mechanism for transporting heat.

Although this invention has been shown and described with respect to detailed embodiments thereof, it will be understood by those skilled in the art that various changes in form and detail may be made without departing from the spirit and scope of the claimed invention.

I claim:

1. An enhanced vaporization/condensation type of heat pipe comprising a closed-circuit fluid conduit having a heat source position at a first temperature in heat exchange relation with a heat source and a heat sink position in heat exchange relation with a heat sink, said heat sink position being at a second temperature lower than said first temperature, first and second catalyst means within the conduit substantially at the heat source and the heat sink positions respectively, and a transport fluid within the conduit, said transport fluid being selected to enter said heat source position as a liquid and to be vaporized thereat, said vaporized transport fluid being reversibly, endothermically at least partially reacted catalytically to thereby reduce the vapor pressure of said transport fluid and enhance said vaporization of said fluid and to provide at least some reaction product, the thermal energy absorbed from the heat source by vaporization of said transport fluid being

| | | Conventional Case | | | Reaction Enhanced Case | | | | |
|---|---|---|---|---|---|---|---|---|---|
| Source Temp (°K.) | Sink Temp (°K.) | Pressure (atm) | Vap Rate (arb) | Heat Transport Rate (arb) | Total Pressure (atm) | Isobutane Pressure (atm) | Vap Rate (arb) | Heat Transport Rate (arb) | Enhancement |
| 320 | 300 | 5.82 | 1.014 | 1.014 | 8.5 | 5.724 | 1.112 | 1.23 | 21% |
| 350 | 300 | 5.87 | 8.61 | 8.61 | 8.5 | 5.30 | 9.18 | 10.29 | 20% |
| 320/350 | 300 | 5.59 | 1.25 | 1.25 | 8.5 | 5.30 | 1.54 | 1.54/1.73 | 23%/35% |
| 320/400 | 300 | 5.34 | 1.50 | 1.50 | 8.5 | 4.68 | 2.15 | 2.15/2.53 | 43%/69% |
| 350/450 | 300 | 5.69 | 8.79 | 8.79 | 8.5 | 4.18 | 10.30 | 10.30/11.92 | 17%/36% |

From the table above, it is seen that for relatively small differences between source and sink temperatures, i.e. ΔT=20°−50° K., the reaction-enhanced case is capable of transporting heat at a 20% faster rate than the conventional case at the same temperatures. The increase in the heat transport rate of reaction-enhanced case over the conventional case is provided both by an increased vaporization rate and by the heat of reaction. It will be appreciated, however, that the contribution by the heat of reaction to the total heat transported is relatively small, such that the heat transported by the heat of vaporization of the isobutane comprises more than 80% of the total heat transported.

The third, fourth and fifth examples in the foregoing Table represent additional heating of the source catalyst 54 beyond the source temperature to shift the equilibrium point of the reaction and thereby promote a more complete reaction while minimizing the degradation in quality of the heat transported. The secondary values in the first column of the Table are catalyst temperatures. The secondary values in the last two columns of the Table represent heat transport rates and enhancements respectively resulting from heat supplied at both temperatures. An optional source of heat, represented by the dotted box 60 in FIG. 3, would be required to heat at least fifty percent of the total thermal energy removed from the heat source by the transport fluid, said reaction product and any remaining vaporized transport fluid being transported to said heat sink position, said reaction product being exothermically reacted catalytically at said heat sink position to reform transport fluid, any said vaporized transport fluid being condensed at the heat sink position thereby to release thermal energy to the sink and return the transport fluid to the liquid form, and the liquid transport fluid being returned to the heat source position for completing and repeating the cycle.

2. The heat pipe of claim 1 wherein said significant portion is at least about 80%.

3. The heat pipe of claim 1 wherein the difference between said first and second temperatures is in the range of about 20°–80° K.

4. The heat pipe of claim 1 wherein said transport fluid is isobutane and said reaction product is n-butane.

5. The heat pipe of claim 4 wherein said first temperature is in the range of about 280°–380° K.

6. The heat pipe of claim 1 wherein the distance between said heat source position and said heat sink position measured through said conduit is less than tens of feet.

7. The heat pipe of claim 1 wherein said vapor transport fluid and said reaction product are transported to said heat sink position by a pressure gradient established substantially by said vaporization/condensation and said chemical reaction cycles.

8. The heat pipe of claim 1 wherein substantially all of said vaporized transport fluid is converted to said reaction product by said reaction at said heat source position.

9. In a heat pipe comprising a closed-circuit fluid conduit having a heat source position at a first temperature in heat exchange relation with a heat source and a heat sink position in heat exchange relation with a heat sink, said heat sink position being at a second temperature lower than said first temperature, first and second catalyst means within the conduit substantially at the source and sink position respectively and a transport fluid within the conduit, the method of operating a heat pipe in a reaction-enhanced vaporization/condensation mode comprising:

supplying said transport fluid in liquid form to said heat source position for vaporization thereat;

reversibly endothermically at least partially reacting catalytically said vaporized transport fluid substantially at said heat source position to thereby reduce the vapor pressure of said transport fluid and enhance said vaporization, said endothermic reaction providing at least some reaction product and said transport fluid being selected such that at least fifty percent of the total thermal energy removed from the heat source by the transport fluid is by vaporization of said transport fluid;

transporting said reaction product and any remaining vaporized transport fluid to said heat sink position;

exothermically catalytically reacting said reaction product substantially at said heat sink position to reform transport fluid;

condensing any said vaporized transport fluid at the heat sink position thereby to release thermal energy to the sink and return the transport fluid to the liquid form; and transporting said liquid transport fluid to said heat source position for completing and repeating the cycle.

10. The method of claim 9 wherein at least about 80 percent of the total thermal energy removed from the heat source by the transport fluid is by vaporization of said transport fluid.

11. The method of claim 9 wherein the difference between said first and second temperatures is in the range of 20°-80° K.

12. The method of claim 9 wherein said transport fluid is isobutane and said reaction product is n-butane.

13. The method of claim 9 wherein said transporting of said transport fluid and said reaction product to said heat sink position is by a pressure gradient established substantially by said vaporization/condensation and said chemical reaction cycles.

14. The method of claim 9 wherein substantially all of said vaporized transport fluid is converted to said reaction product by said endothermic reaction at said heat source position.

15. The method of claim 9 including the further step of heating said first catalyst means to a third temperature higher than said first temperature to react a greater portion of said vaporized transport fluid than is possible at said first temperature alone.

16. An enhanced vaporization/condensation type of heat pipe comprising a closed-circuit fluid conduit having a heat source position at a first temperature in heat exchange relation with a heat source and a heat sink position in heat exchange relation with a heat sink, said heat sink position being at a second temperature lower than said first temperature, first and second catalyst means within the conduit substantially at the heat source and the heat sink positions respectively, and a transport fluid within the conduit, said transport fluid being isobutane, said transport fluid being selected to enter said heat source position as a liquid and to be vaporized thereat, said vaporized transport fluid being reversibly, endothermically at least partially reacted catalytically to thereby reduce the vapor pressure of said transport fluid and enhance said vaporization of said fluid and to provide at least some reaction product, said reaction product being n-butane, said reaction product and any remaining vaporized transport fluid being transported to said heat sink position, said reaction product being exothermically reacted catalytically at said heat sink position to reform transport fluid, any said vaporized transport fluid being condensed at the heat sink position thereby to release thermal energy to the sink and return the transport fluid to the liquid form, and the liquid transport fluid being returned to the heat source position for completing and repeating the cycle.

17. The heat pipe of claim 16 wherein the difference between said first and second temperatures is in the range of about 20°-80° K.

18. In a heat pipe comprising a closed-circuit fluid conduit having a heat source position at a first temperature in heat exchange relation with a heat source and a heat sink position in heat exchange relation with a heat sink, said heat sink position being at a second temperature lower than said first temperature, first and second catalyst means within the conduit substantially at the source and sink position respectively and a transport fluid within the conduit, the method of operating a heat pipe in a reaction-enhanced vaporization/condensation mode comprising:

supplying said transport fluid in liquid form to said heat source position for vaporization thereat, said transport fluid being isobutane;

reversibly endothermically at least partially reacting catalytically said vaporized transport fluid substantially at said heat source position to thereby reduce the vapor pressure of said transport fluid and enhance said vaporization, said endothermic reaction providing at least some reaction product, said reaction product being n-butane;

transporting said reaction product and any remaining vaporized transport fluid to said heat sink position;

exothermically catalytically reacting said reaction product substantially at said heat sink position to reform transport fluid;

condensing any said vaporized transport fluid at the heat sink position thereby to release thermal energy to the sink and return the transport fluid to the liquid form; and transporting said liquid transport fluid to said heat source position for completing and repeating the cycle.

19. The method of claim 18 wherein the difference between said first and second temperatures is in the range of 20°-80° K.

* * * * *